US006866418B2

(12) United States Patent
Pillai et al.

(10) Patent No.: US 6,866,418 B2
(45) Date of Patent: Mar. 15, 2005

(54) C-ARM X-RAY APPARATUS FOR INCREASED OVERSCAN

(75) Inventors: Vipin J. Pillai, Karnataka State (IN); Bindu Philip, Karnataka (IN); Amol Gupta, Karnataka (IN); Ratanjit Singh Sohal, Punjab (IN)

(73) Assignee: General Electric Company, Schenectady, NY (US)

(*) Notice: Subject to any disclaimer, the term of this patent is extended or adjusted under 35 U.S.C. 154(b) by 246 days.

(21) Appl. No.: 10/241,096

(22) Filed: Sep. 11, 2002

(65) Prior Publication Data

US 2004/0047450 A1 Mar. 11, 2004

(51) Int. Cl.[7] ............................................... H05G 1/02
(52) U.S. Cl. ...................................... 378/198; 378/195
(58) Field of Search ................................. 378/195–198

(56) References Cited

U.S. PATENT DOCUMENTS 4,209,706 A * 6/1980 Nunan ........................ 378/189
6,609,826 B1 * 8/2003 Fujii et al. .................. 378/198

* cited by examiner

*Primary Examiner*—Craig E. Church
(74) *Attorney, Agent, or Firm*—Joseph S. Heino; Patrick M. Bergin; Henry Policinski

(57) ABSTRACT

A C-arm x-ray machine includes a compact yoke and a support arm interposed between the yoke and the support base to reduce overall length of the machine and to increase overscan. The support arm is designed to lower the axis of rotation such that the axis of rotation nearly coincides with the center of gravity of the C-arm. The compact yoke is designed with a thin pivot point and includes a steel sleeve to enclose a pin situated at the first end of the yoke. The steel sleeve is required to strengthen the yoke at the critical load bearing area near the first end of the yoke.

23 Claims, 17 Drawing Sheets

C-ARM X-RAY APPARATUS FOR INCREASED OVERSCAN

BACKGROUND OF THE INVENTION

1. Field of the Invention

The present invention relates generally to the field of x-ray imaging machines and systems. More specifically, the present invention pertains to a C-arm x-ray imaging machine incorporating new and improved mechanisms for adjustment and control of the C-arm including a compact yoke for increased overscan.

2. Background of the Invention

It is frequently desired to X-ray a patient from several different positions and is often preferable to do so without the need to reposition the patient. Mobile C-arm x-ray diagnostic equipment, such as that shown in FIG. 1 has been developed to meet these needs and is now well known in the medical and surgical arts. The C-arm x-ray machine is especially useful in that it is small enough and mobile enough to be present in an operating or exam situation without requiring the physician or technician to repeatedly move and without requiring the patient to change positions to obtain a suitable image.

The phrase "C-arm" refers to the movable C-shaped member at one end of the machine. The C-arm contains x-ray source and an image receptor mounted on opposing ends of the C-arm such that x-rays emitted by the source are incident on and detected by the detector. The source and the detector are positioned such that when, for example, a human extremity is interposed between the x-ray source and the image receptor and irradiated with x-rays, the receptor produces data representative of characteristics of the interposed object. The data produced is frequently displayed on a monitor or electronically stored.

The C-arm is normally mounted such that it is permitted two degrees of freedom. First, the C-arm track is slidably mounted to a support member so as to be movable in relation to the support member. This permits the x-ray source and image receptor to be moved rotatably about the arc of curvature of the track in the C-arm. The C-arm support member also permits rotation of the C-arm about its axis. Often the support member is in the general shape of an L and is referred to as the yoke. Mobile C-arms have a third degree of freedom in that they are free to move horizontally along the floor and a fourth in that the C-arm can be raised and lowered.

Obviously, a support structure that permits rotation and movement of such a C-arm must be constructed to withstand large torsional, tensile and compressive stresses. It is also desirable to provide a support that is structure that is heavy enough and that has a center of gravity low enough to avoid tipping when the C-arm and yoke are rotated or raised, which in some cases causes a dramatic shift in the center of mass of the machine.

Additionally, C-arm x-ray equipment must be delicately positioned in order to obtain the image or images desired or required by the physician. Unfortunately, the weight of the support structure makes it difficult to position the C-arm. Therefore, it is desirable to design a source of frictional drag between the C-arm and the support member as well as on the C-arm track.

It is also desirable to balance the C-arm, x-ray source, x-ray detector and yoke so that relatively little physical effort is required to move the C-arm about the orbital rotation axis and the lateral rotation axis. One manner of accomplishing this is to design the C-arm such that its center of mass is as close as possible to the orbital and lateral rotational axes.

Some C-arm designs require a center of mass that is separate from the axis of rotation. In these unbalanced designs, the user must exert significant force to rotate the apparatus. This physical exertion generally detracts from other, more significant tasks that a health care provider may be undertaking. Also, unbalanced designs can be dangerous to both the operator and the patient. For example, unbalanced C-arms require much more powerful braking systems. Without an adequate braking system, the C-arm could unexpectedly rotate downwardly and strike an individual. Accordingly, a completely balanced C-arm x-ray imaging system is difficult to design at best.

Previous C-arm x-ray machines required the removal of the C-arm in order to service or replace the brake means. Other C-arms require the user to remove the back of the yoke to repair or replace the brake. Both processes are cumbersome and time consuming. Additionally, prior devices were difficult to maintain sterile environment.

The term "overscan" is the extent to which a C-arm is permitted to rotate beyond the vertical beam configuration. Overscan is limited in machines that are configured with conventional yokes. Customers generally prefer increased overscan because they can image the patient more easily with fewer positional adjustments to the machine. The degree of overscan is generally limited by either the x-ray source or the x-ray detector colliding with the yoke. Design guidelines also require additional clearance on each side of the yoke to avoid the danger of pinch points. In the preferred embodiment, each extra inch of clearance translates to an almost 3 degree difference in overscan.

BRIEF SUMMARY OF THE INVENTION

It is therefore an object of the present invention is to provide a C-arm x-ray apparatus that is either optimally balanced or requires little effort to rotate. A further object of the device of the present invention is to increase the overscan of the apparatus. Another object of the device of the present invention is to maximize bearing span through an improved lip design and designed avoidance of pinch points. It is yet another object of the present invention to provide such a device that requires relatively few parts and can be easily manufactured. It is also an object of this invention to reduce the overall length of the system. It is yet another object of the present invention to provide an aesthetically pleasing device. Yet another object of the device of the present invention is to provide an aseptic device.

The device of the present invention has met these objects. It provides for a new and unique C-arm x-ray apparatus that incorporates a compact yoke. This new yoke contributes to overall length reduction of the machine without any reduction in features or abilities. Overscan of the C-arm is also increased by providing a new interface between the yoke and the C-arm. Additional objects and advantages of the invention will be set forth in the description that follows. Other objects and advantages may be learned by practice of the invention.

DETAILED DESCRIPTION OF THE INVENTION

The following detailed description is intended to describe the preferred embodiments that are depicted in the figures. It is to be understood that changes could be made to that which is specifically described and shown that would still fall within the scope of the present invention.

Figure 5:
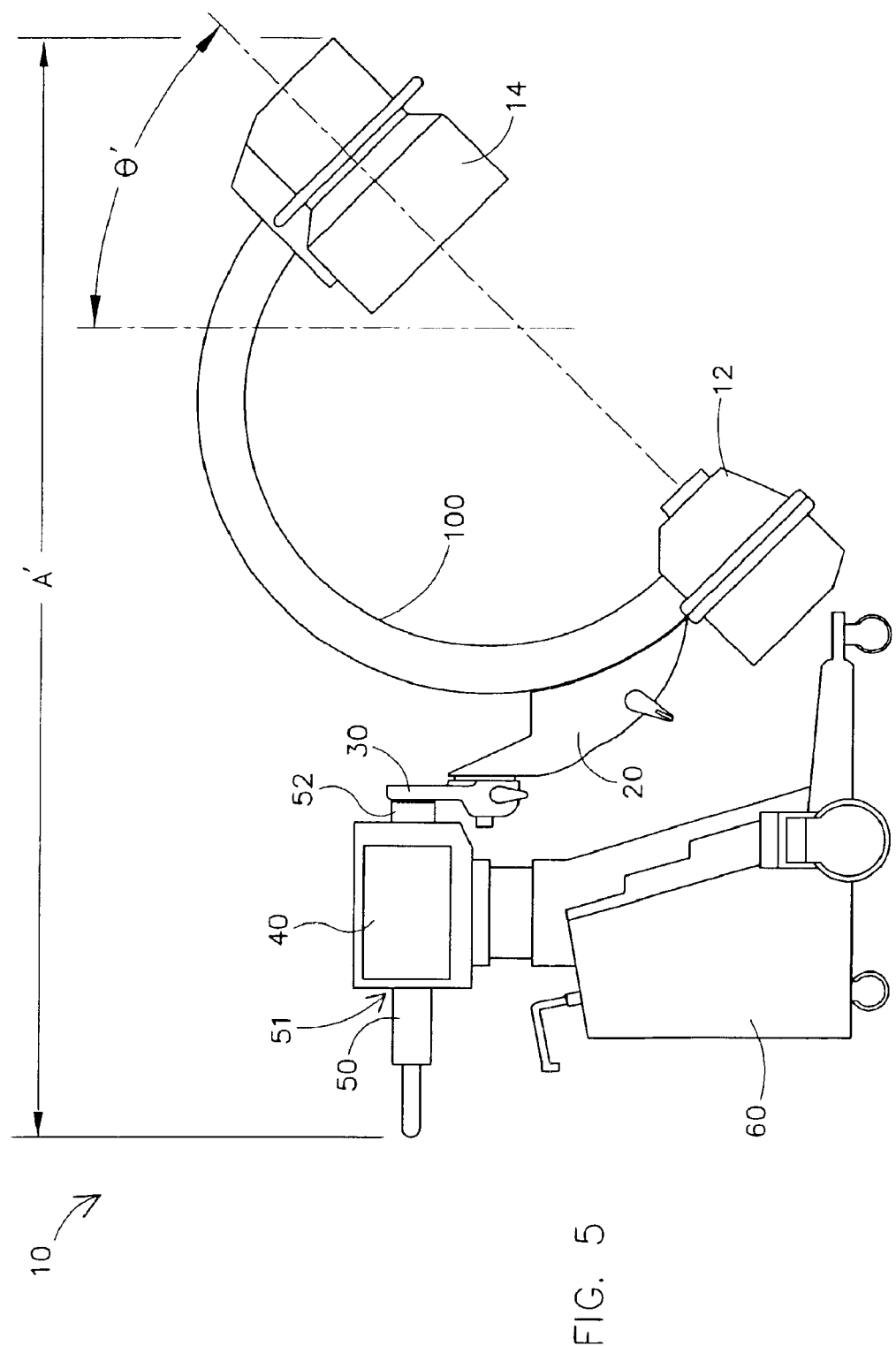
FIG. 5 is a left side elevational view of a C-arm x-ray machine constructed in accordance with the present invention.

Referring now to the drawings in detail, wherein like numbered elements refer to like elements throughout, FIG. 5 depicts the basic components of the imaging system of the present invention. In general, the C-arm x-ray imaging machine, generally identified 10, is comprised of the following components: an x-ray source 12, an image receptor 14, an image processing system, a display and viewing system, a high voltage generator and a control unit.

The x-ray source 12 preferably comprises an x-ray tube and a high-voltage generator. The high-voltage generator is preferably connected to an adjustable high-voltage power supply capable of generating approximately –70 kV to –120 kV. The x-ray source 12 is generally a scanning beam x-ray in which charged particles are scanned across a target assembly. When the system is operated, the charged particle beam strikes the target and generates x-ray photons. The x-ray photons preferably pass through a collimator and form an x-ray beam. The x-ray beam has an axis that is substantially aligned with the center of the active area of the x-ray detector. The x-ray beam has a vector that is defined by the axis of the x-ray beam in the direction of the x-ray detector assembly.

The imaging object is generally the patient or some portion of the patient. X-rays that have passed through the patient are detected and later processed for some form of interpretation.

The detection and recording system is generally comprised of the image receptor 14. The image receptor captures the x-ray photons scanned across the imaging object and converts them to electrical signals. The impulses are then converted to digital data and either stored or fed immediately into a computer for image reconstruction. The imaging process system generally consists of a computer with a software package that reconstructs the image and displays the image on a screen and a device that provides for storage of the image.

The display system and the control unit may be remotely operated. Thus the operator can be shielded from radiation but still perform the x-ray. Alternatively, the entire system can be placed in an examining or operating room so that the health care provider can view images of the patient in real time.

The mobile c-arm x-ray imaging machine, generally identified 10, includes a wheeled support base 60. In a preferred embodiment the support base 60 is a generally rectangular upright body that may be equipped with one or more video monitors and has an upper portion or doghouse 40 with an extendable cross arm 50. The extendable cross arm 50 has a first portion 51 slidably mounted within the doghouse 40 and a second end 52 having an aperture defined in the end of the cross arm 50. The support base 60 is important to the imaging machine 1 in that it provides a platform for the yoke 20 and the C-arm 100. Therefore, the support base 60 should have a footprint large enough such that the yoke 20 and C-arm 100 are permitted to rotate without the danger of tipping and/or the support base 60 must be heavy enough to prevent tipping of the C-arm x-ray machine 1.

The device of the present invention, unlike previous devices provides a support arm 30 between the yoke 20 and the support base 60. The support arm 30 is designed to lower the axis of rotation such that the axis of rotation coincides, or very nearly coincides with the center of gravity of the C-arm 100. The closer the center of gravity of the C-arm 100 to the C-arm's 10 axis of rotation, the smaller the force required to rotate the C-arm 100.

Figure 1:
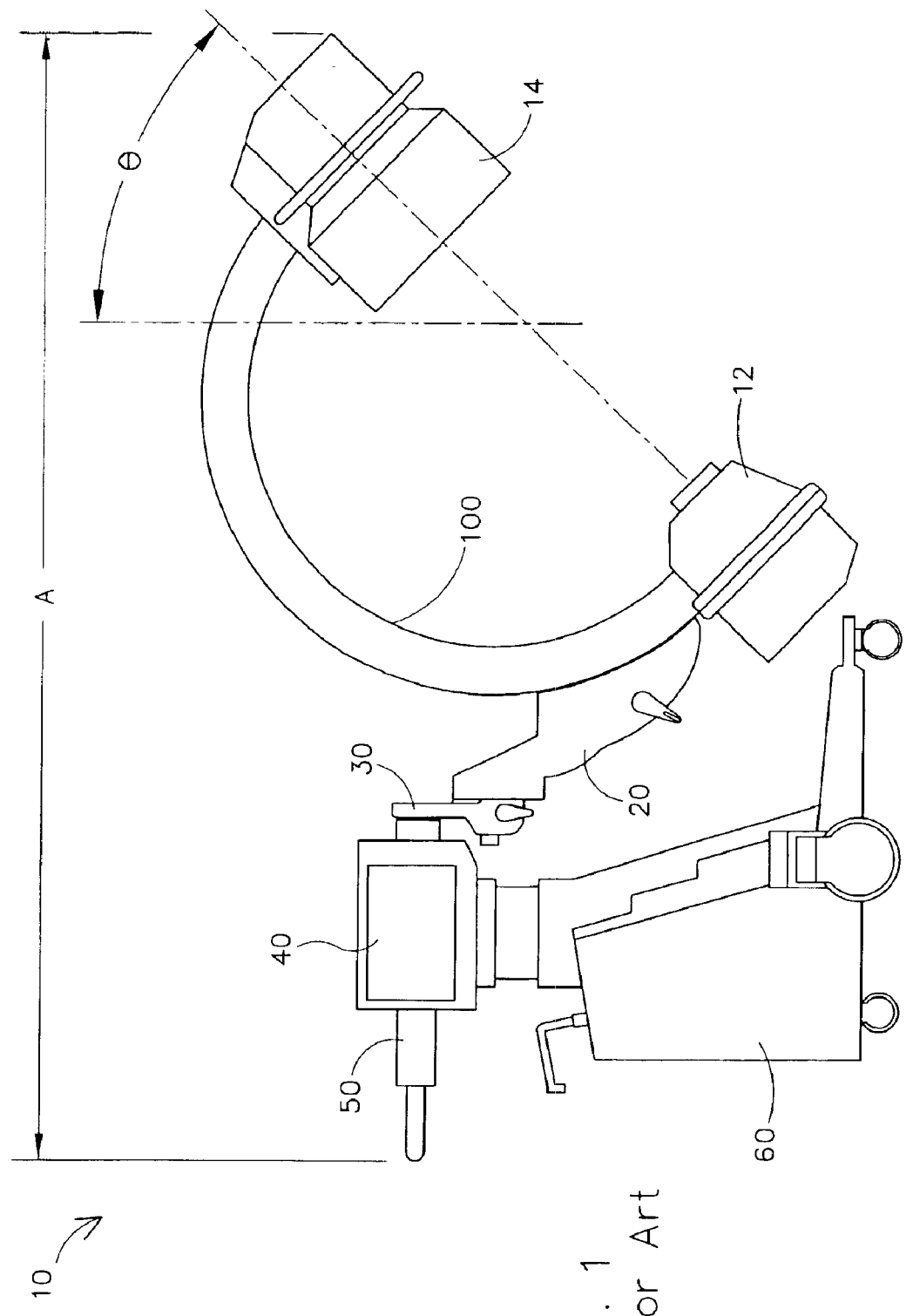
FIG. 1 is a left side elevational view of a prior art C-arm x-ray machine.
Figure 2:
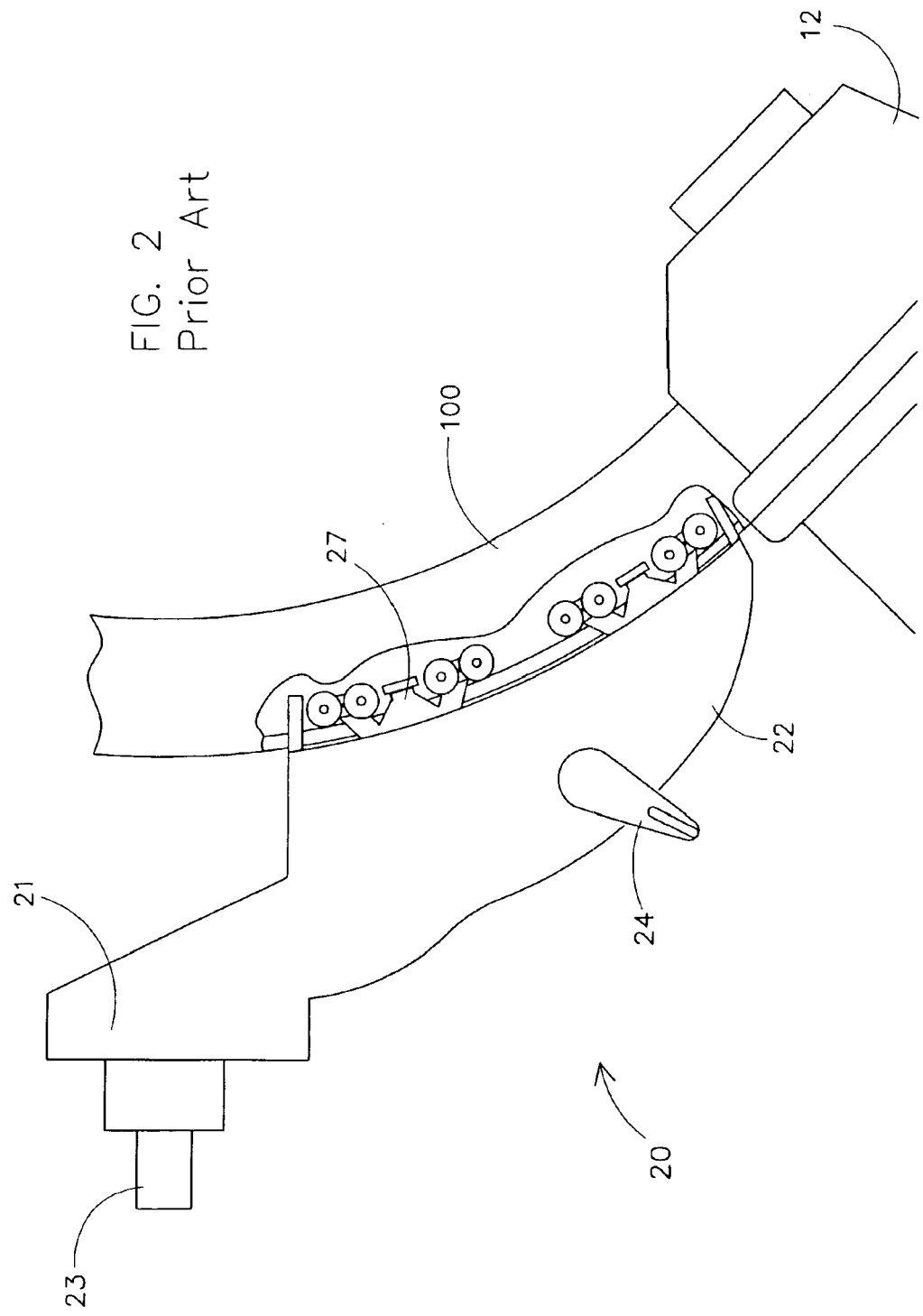
FIG. 2 is an enlarged an partially segmented left side elevational view of a typical yoke and x-ray imager employed in a prior art C-arm x-ray machine.

The yoke 20 is attached at its first end 21 to the support arm 30 and at its second end 22 to the C-arm 100. Obviously, the yoke 20 must be able to withstand a wide variance in forces not only as the C-arm 100 is moved along the yoke 20, but also as the C-arm 100 is rotated. Additionally, the yoke 20 must be an item of relatively low weight despite design guidelines requiring a relatively high factor of safety. Low weight is a requirement for the design so that the C-arm 100 can be easily repositioned during an examination. Prior designs as shown in FIG. 1 and emphasized in FIG. 2 have provided for an extremely bulky yolk 20, which weighed more and further unbalanced the C-arm 100 and caused greater strain and wear on the brake in the support arm 30, which controls the rotation of the C-arm 100. In comparison with prior devices, the present invention provides for a new and unique yoke 20 of composite design, as shown in FIG. 6, which is much more compact.

Figure 6:
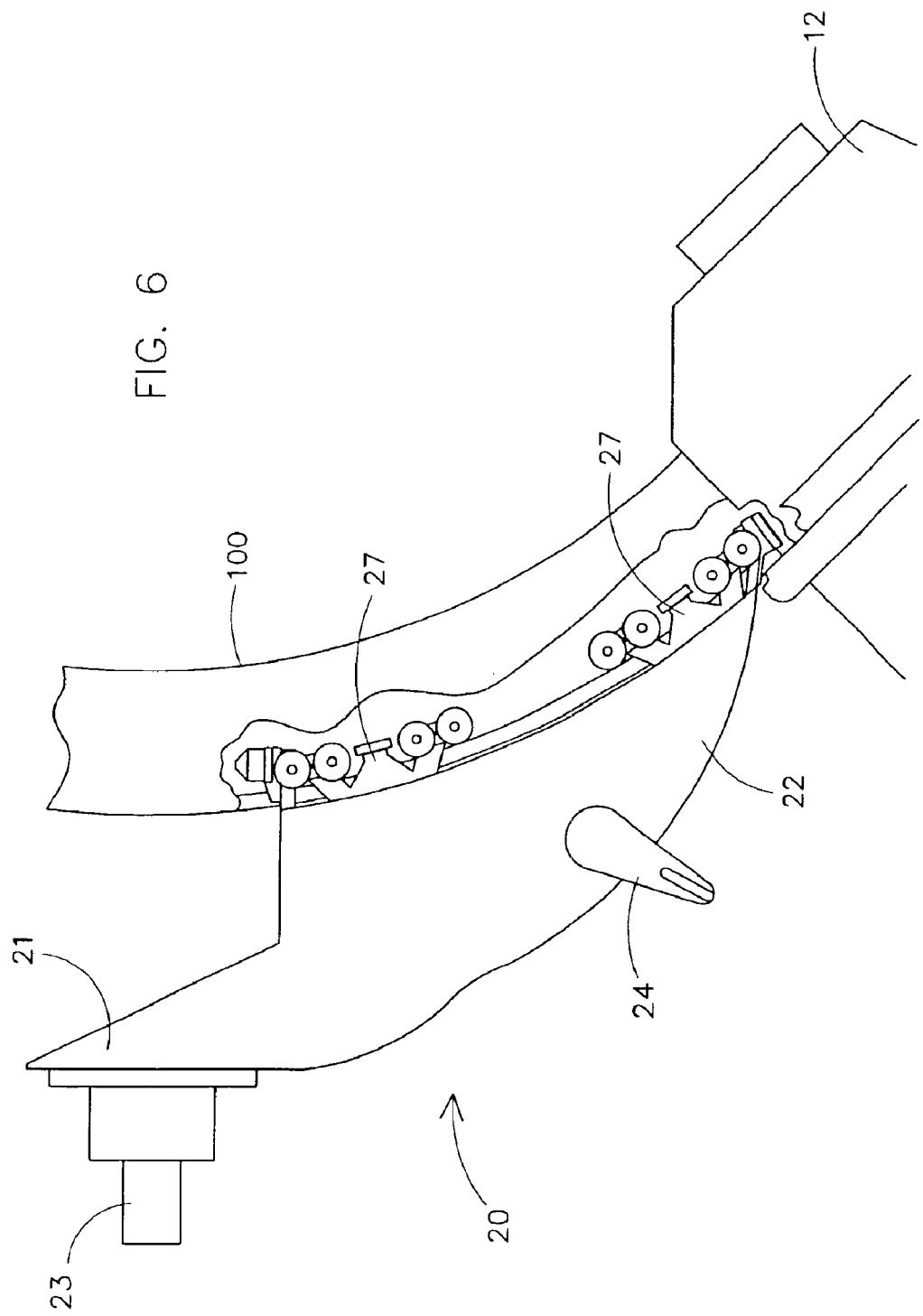
FIG. 6 is an enlarged and partially segmented left side elevational view of the x-ray imager and the yoke used in the present invention.

The yoke 20, as pictured in FIGS. 5 and 6, has a first end 21 attached to the support arm 30 and a second end 22 attached to the C-arm. As the C-arm 100 is an overhanging part, strength of the yoke 20 and the safety of patients and healthcare workers is an issue. Therefore, a relatively high safety factor is used. The requirement for a high factor of safety in addition to the requirement that the yoke be lightweight led designers to choose an aluminum alloy for the part. Unfortunately, use of the aluminum instead of steel for the yoke 20 requires building a bulky yoke 20. Narrowing the yoke 20 in order to reduce the space requirements of the machine in general required strengthening the yoke 20 beyond the capacity of aluminum.

Figure 8:
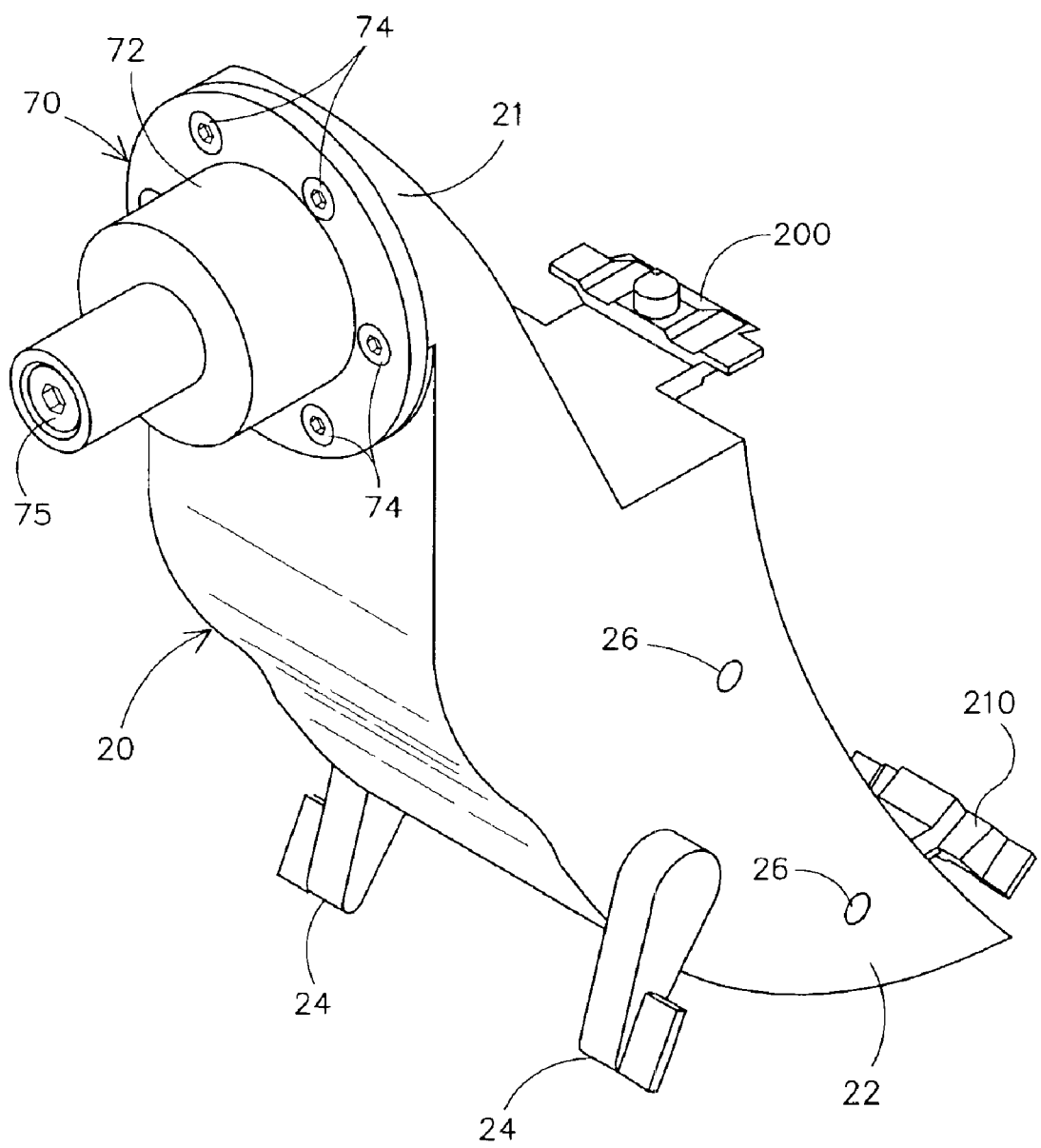
FIG. 8 is a top, left and rear perspective view of the yoke used in the present invention.
Figure 9:
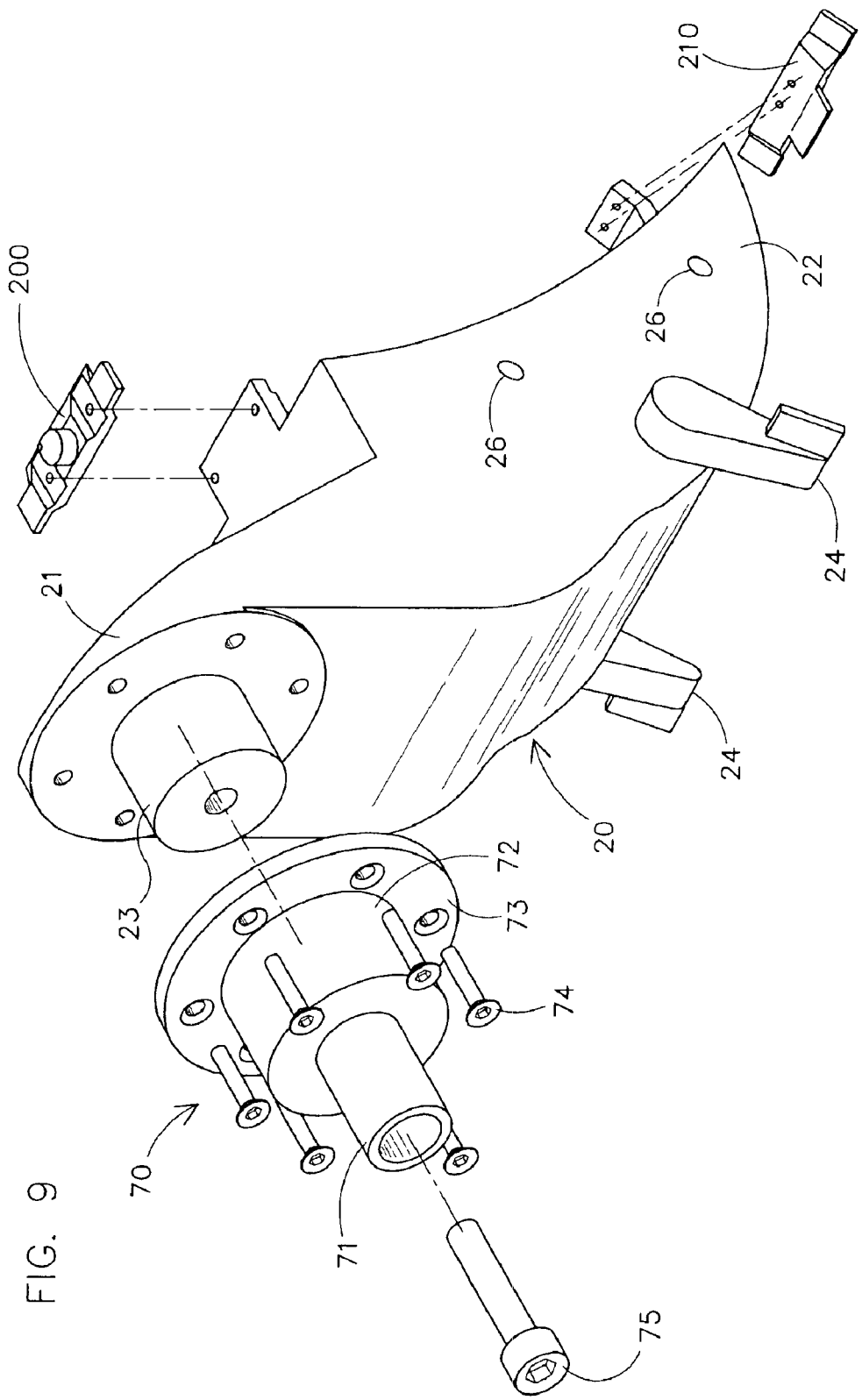
FIG. 9 is a top, left and rear perspective view of the yoke illustrated in FIG. 8 and also showing an exploded view of the steel sleeve, the imager lip and the TTH lip.
Figure 10A:
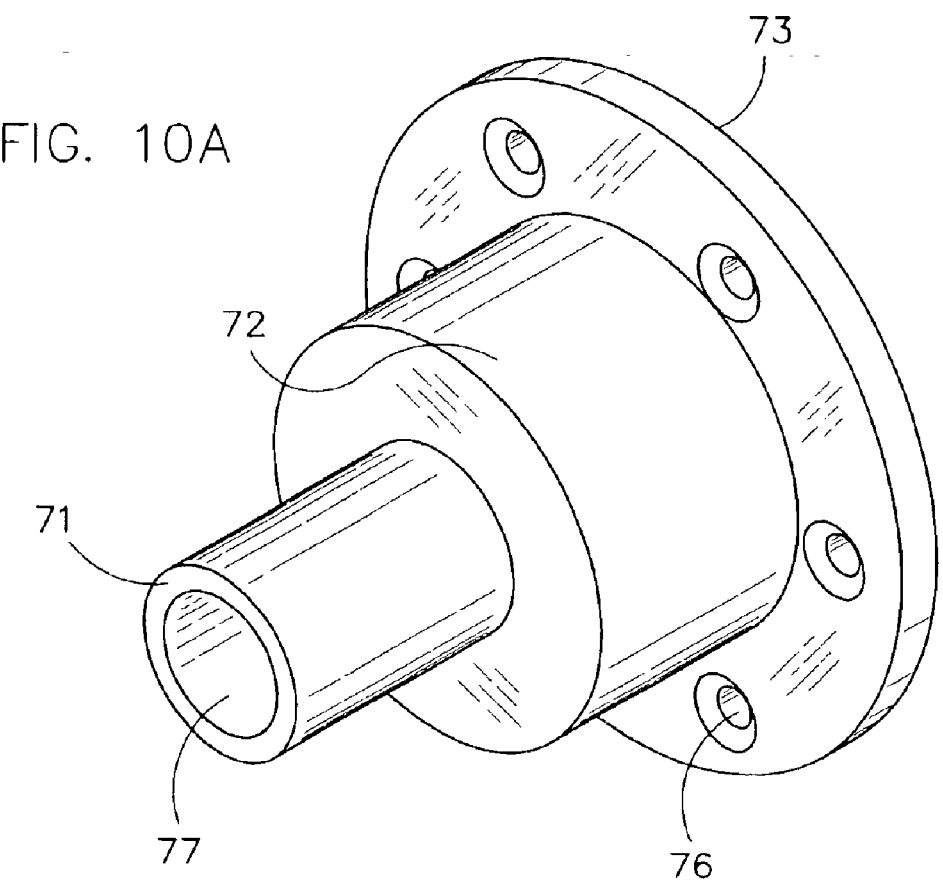
FIG. 10A is a further enlarged top, left and rear perspective view of the steel sleeve used to reinforce the aluminum yoke of the present invention.
Figure 10B:
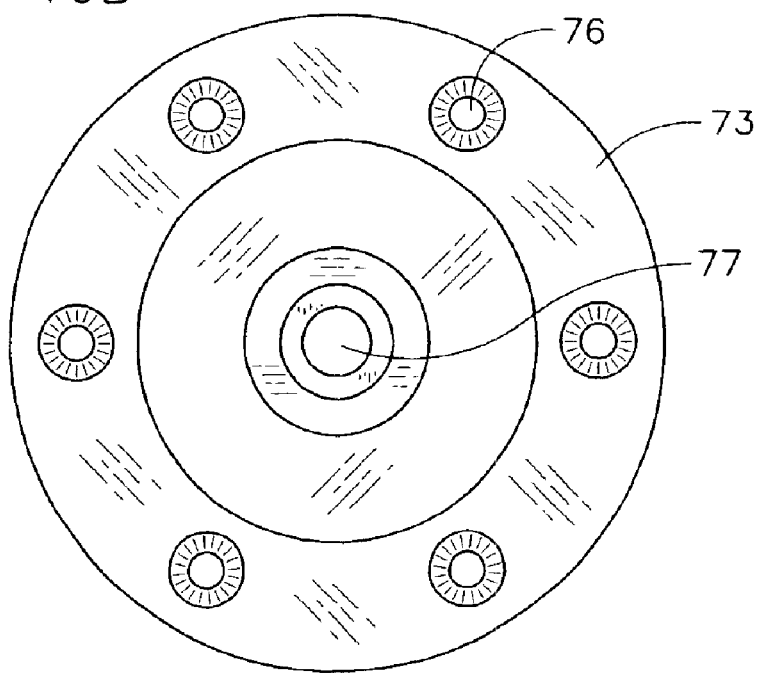
FIG. 10B is a rear elevational view of the steel sleeve illustrated in FIG. 10A.
Figure 10C:
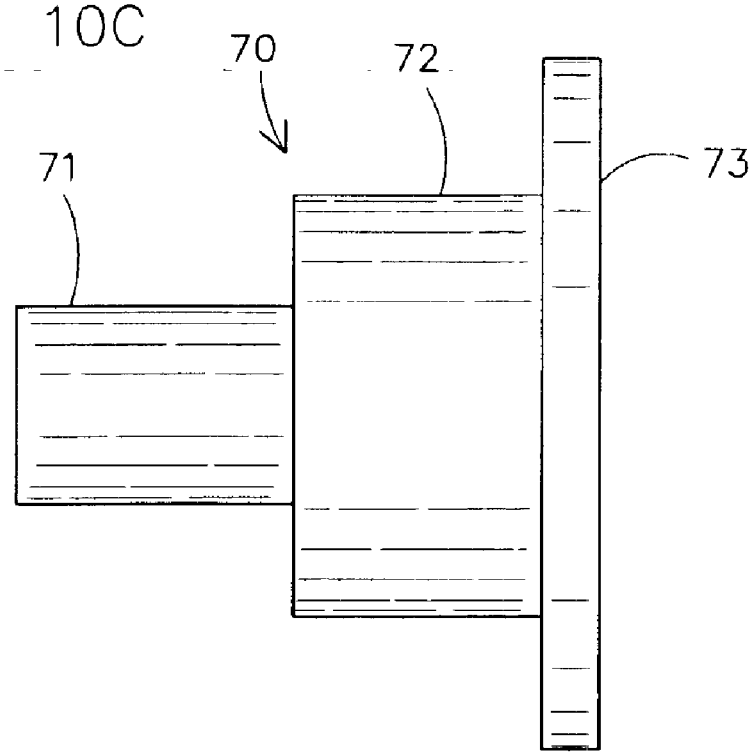
FIG. 10C is a left side elevational view of the steel sleeve illustrated in FIG. 10A.
Figure 10D:
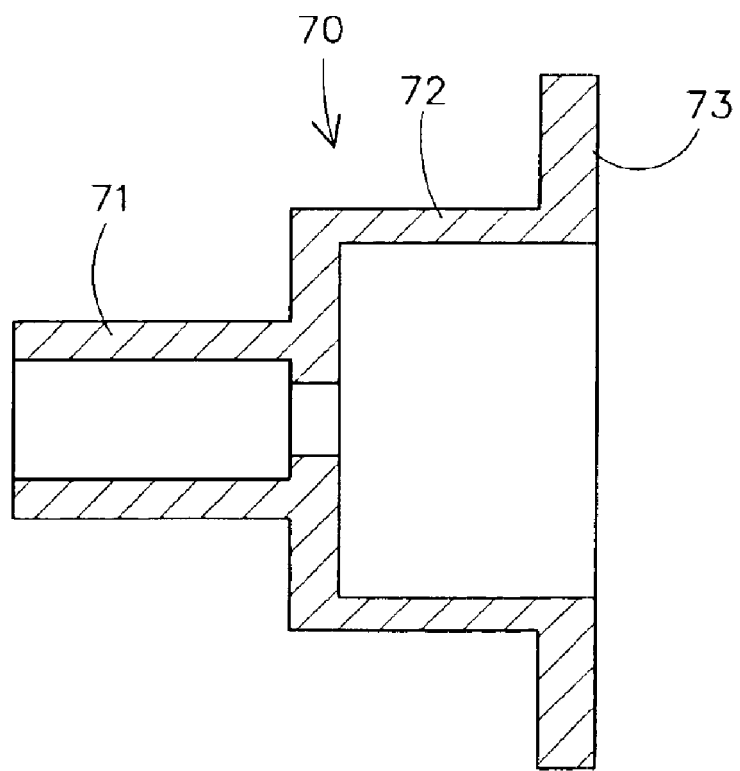
FIG. 10D is a left side sectional view of the steel sleeve illustrated in FIG. 10A.
Figure 11A:
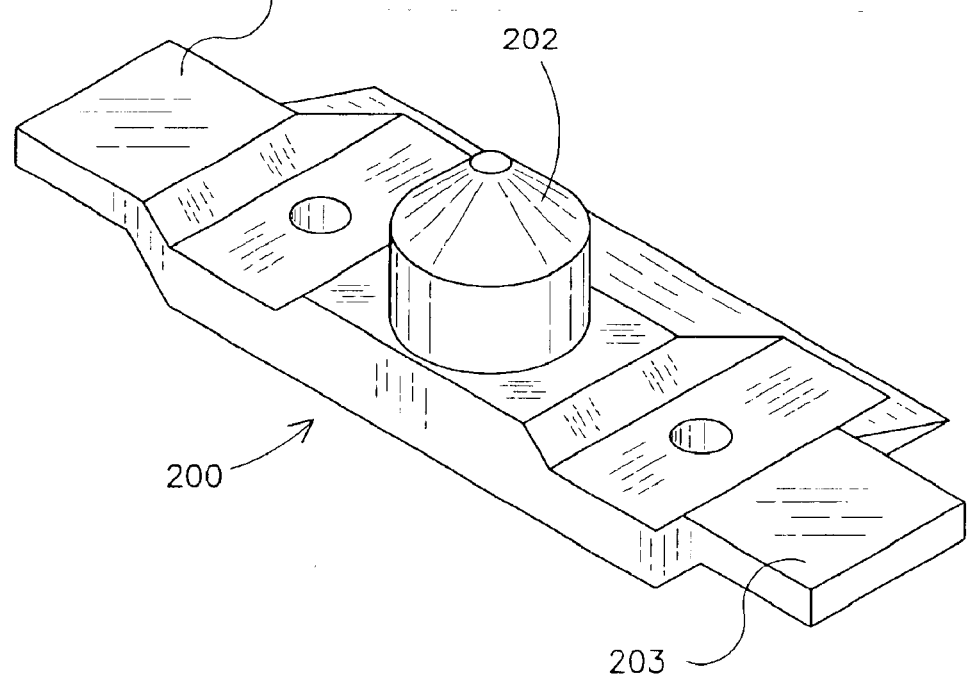
FIG. 11A is a further enlarged front, top and left side perspective view of the imager lip of the present invention.
Figure 11B:
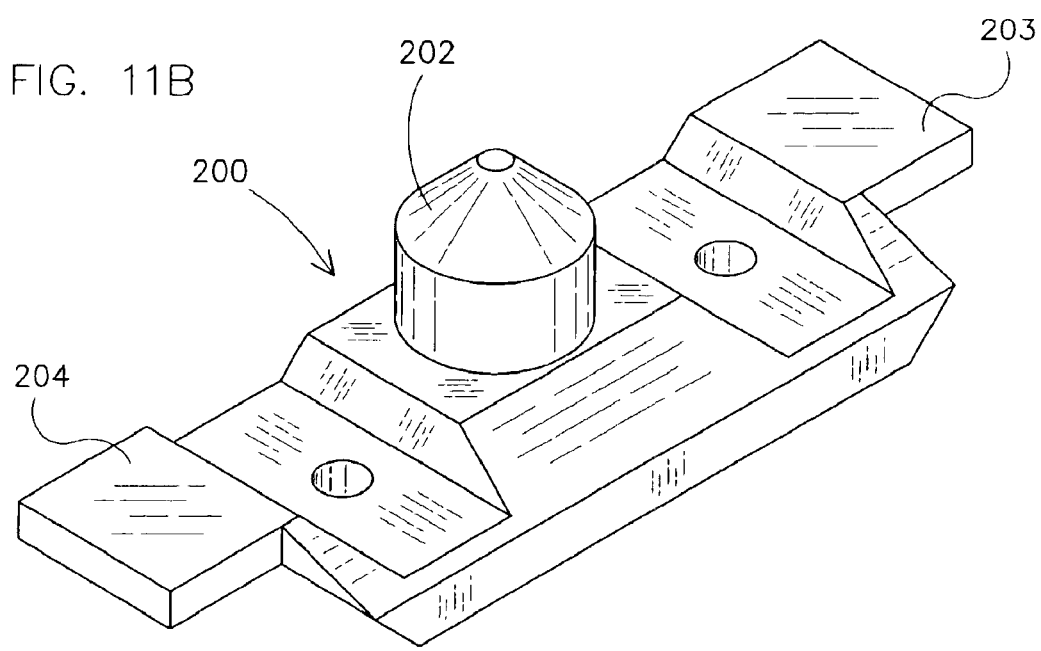
FIG. 11B is a front, top and right side perspective view of the imager lip illustrated in FIG. 11A.
Figure 11C:
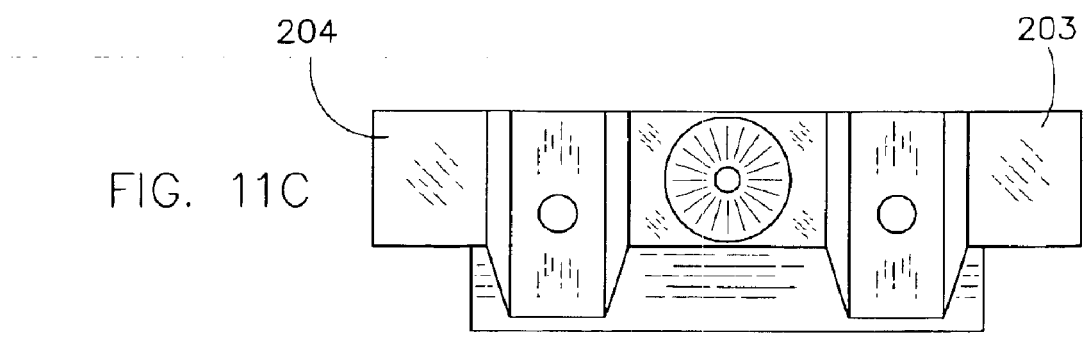
FIG. 11C is a top plan view of the imager lip illustrated in FIG. 11A.
Figure 11D:
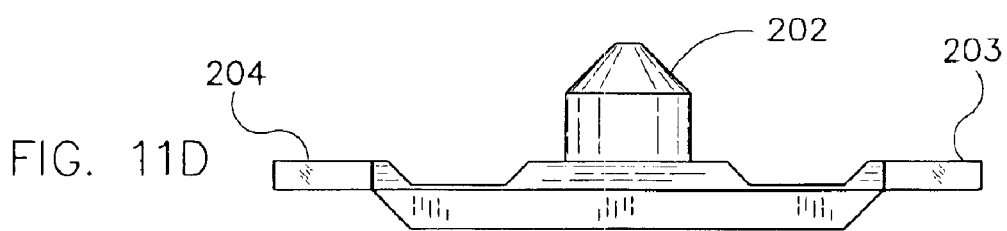
FIG. 11D is a front elevational view of the imager lip illustrated in FIG. 11A.
Figure 11E:
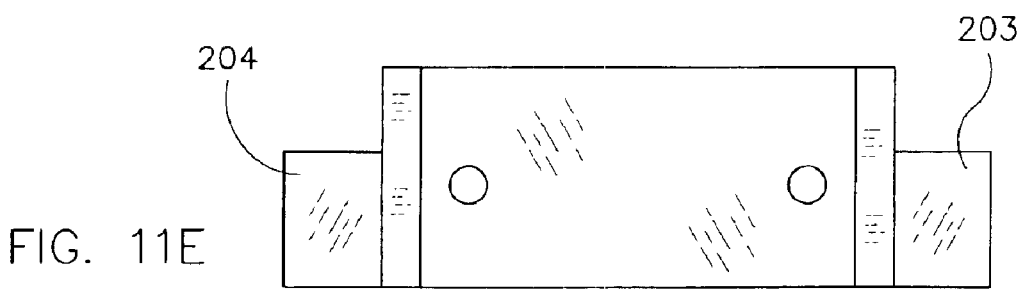
FIG. 11E is a bottom plan view of the imager lip illustrated in FIG. 11A.
Figure 11F:
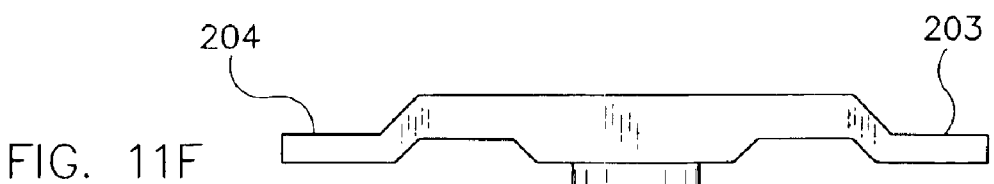
FIG. 11F is a rear elevational view of the imager lip illustrated in FIG. 11A.
Figure 11G:
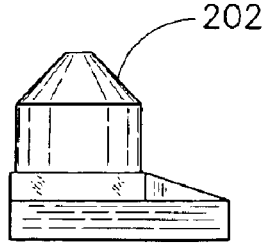
FIG. 11G is a left side elevational view of the imager lip illustrated in FIG. 11A.
Figure 11H:
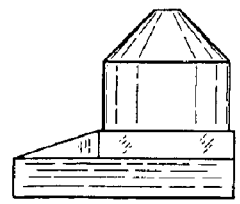
FIG. 11H is a right side elevational view of the imager lip illustrated in FIG. 11A.
Figure 12A:
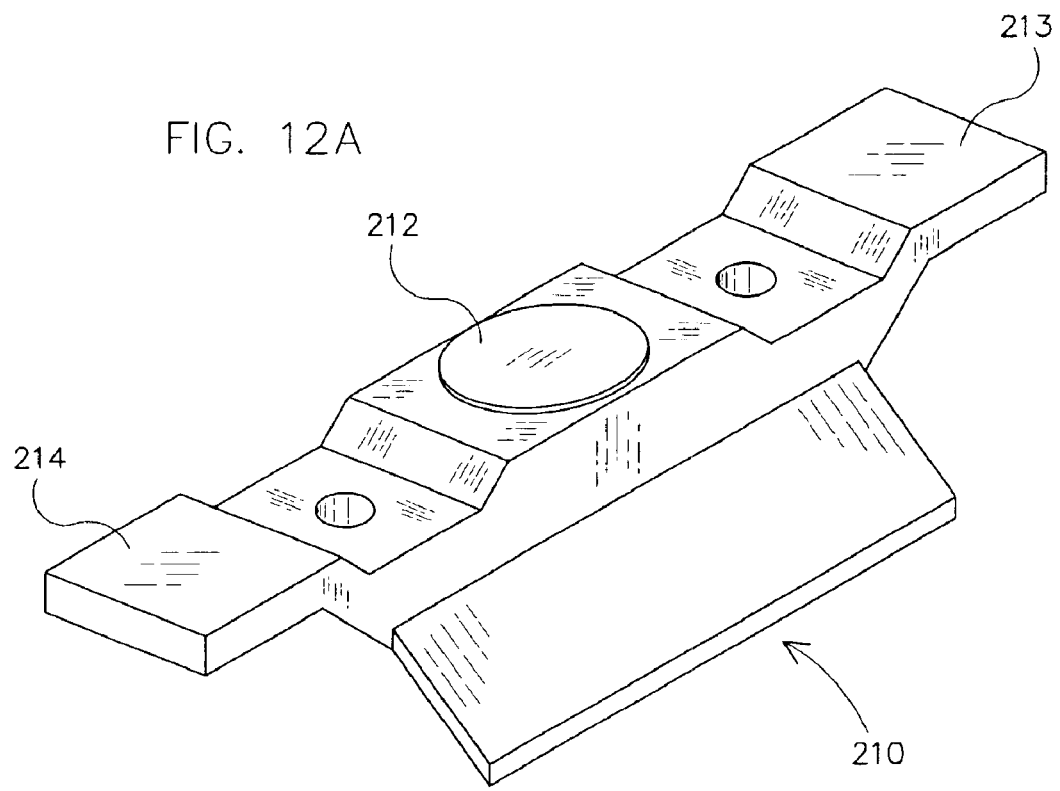
FIG. 12A is a further enlarged front, left and top perspective view of the TTH lip of the present invention.
Figure 12B:
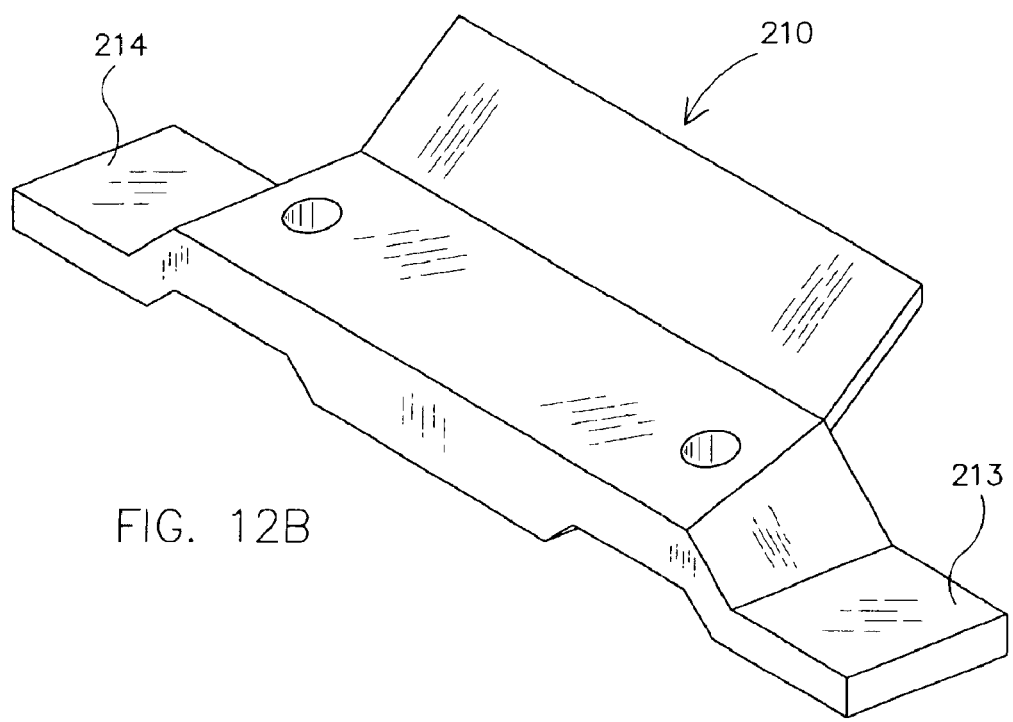
FIG. 12B is a rear, front and bottom perspective view of the TTH lip illustrated in FIG. 12A.
Figure 12C:
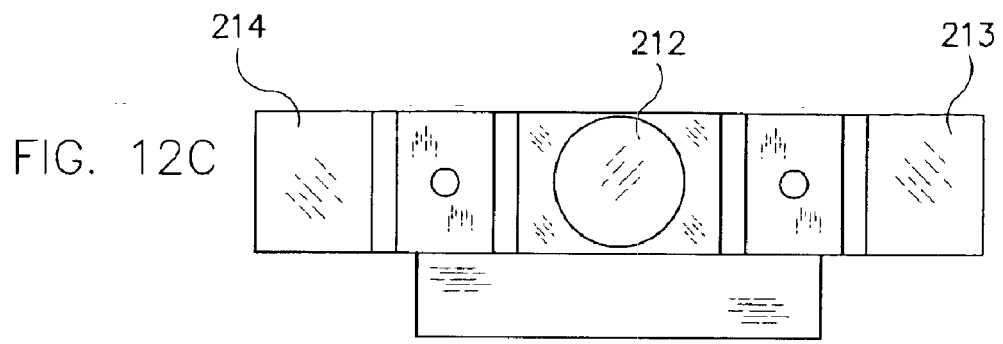
FIG. 12C is a bottom plan view of the TTH lip illustrated in FIG. 12A.
Figure 12D:
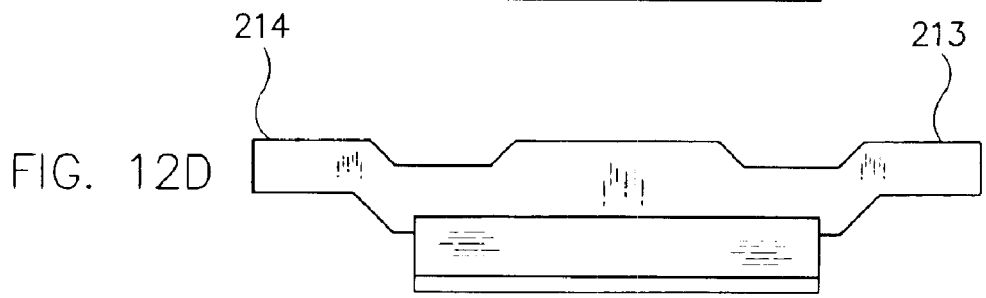
FIG. 12D is a front elevational view of the TTH lip illustrated in FIG. 12A.
Figure 12E:
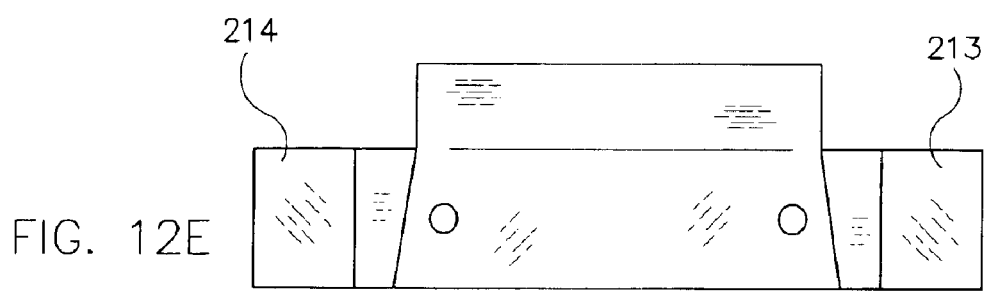
FIG. 12E is a top plan view of the TTH lip illustrated in FIG. 12A.
Figure 12F:
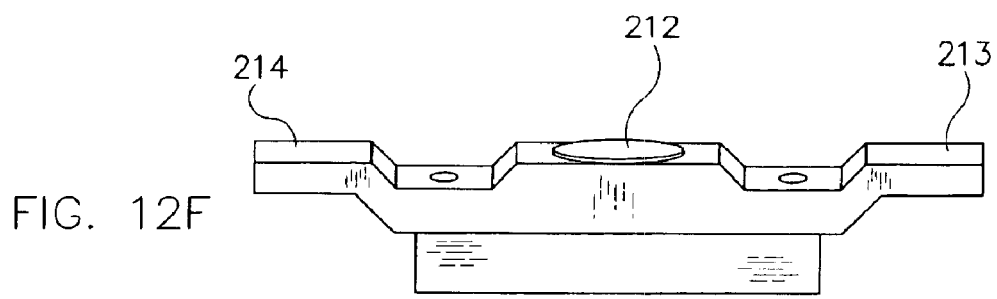
FIG. 12F is a rear elevational view of the TTH lip illustrated in FIG. 12A.
Figure 12G:
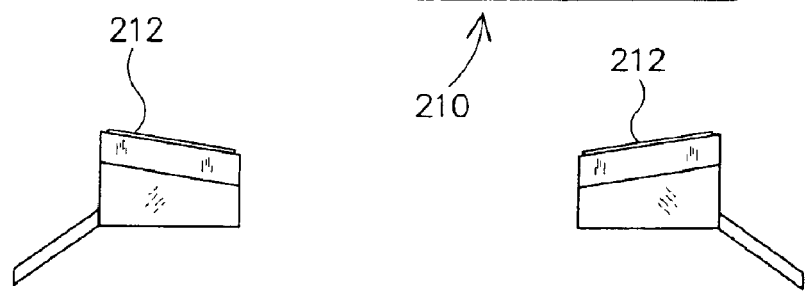
FIG. 12G is a right elevational view of the TTH lip illustrated in FIG. 12A.
Figure 12H:
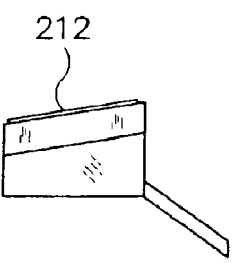
FIG. 12H is a left elevational view of the TTH lip illustrated in FIG. 12A.

In order to strengthen the yoke 20, the present invention provides for a steel sleeve 70, shown in FIG. 8, to enclose the pin 23 at the first end 21 of the yoke 20. An exploded view of the same steel sleeve 70 is shown in FIG. 9 As can be observed from FIG. 9, the sleeve 70 is attached to the yoke 20 and mounts over a stub 23 in the first end 21 of the yoke 20. The steel sleeve 20 is required to strengthen the yoke 20 at the critical load bearing area near the first end 21 of the yoke 20. FIGS. 10A through 10D further illustrate the details of the sleeve 70 of the present invention.

As is shown in FIG. 10A through FIG. 10d and overall in FIG. 9, the pin 23 on the first end 21 of the yoke 20 is generally cylindrical in shape. The sleeve 70 can be generally thought of as a cylinder having a first end 71 and a second open end 72 that slides snugly over the pin 23. The steel sleeve 70 is mounted to the aluminum yoke 20 using bolts, although other means of attachment are possible. The bolts 74 insert through apertures 76 in the skirt to connect the skirt 73 of the sleeve 70 to the first end of the yoke 21. The sleeve 70 is also generally attached to the yoke 20 through the pin using a bolt 75, or other means of attachment, through the aperture 77 in the first end 77 of the sleeve 70.

Figure 13A:
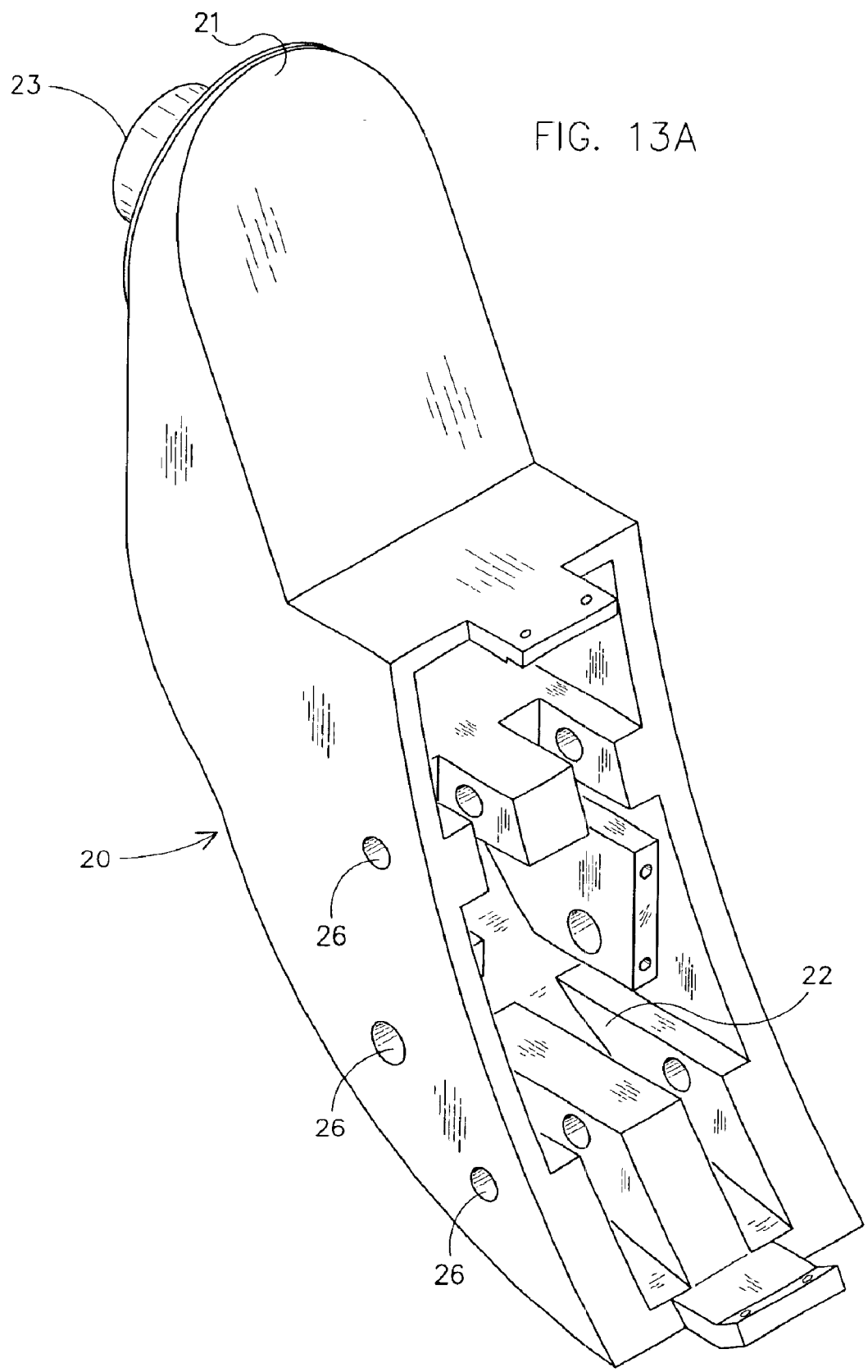
FIG. 13A is a further enlarged top, front and left perspective view of the yoke of the present invention.
Figure 13B:
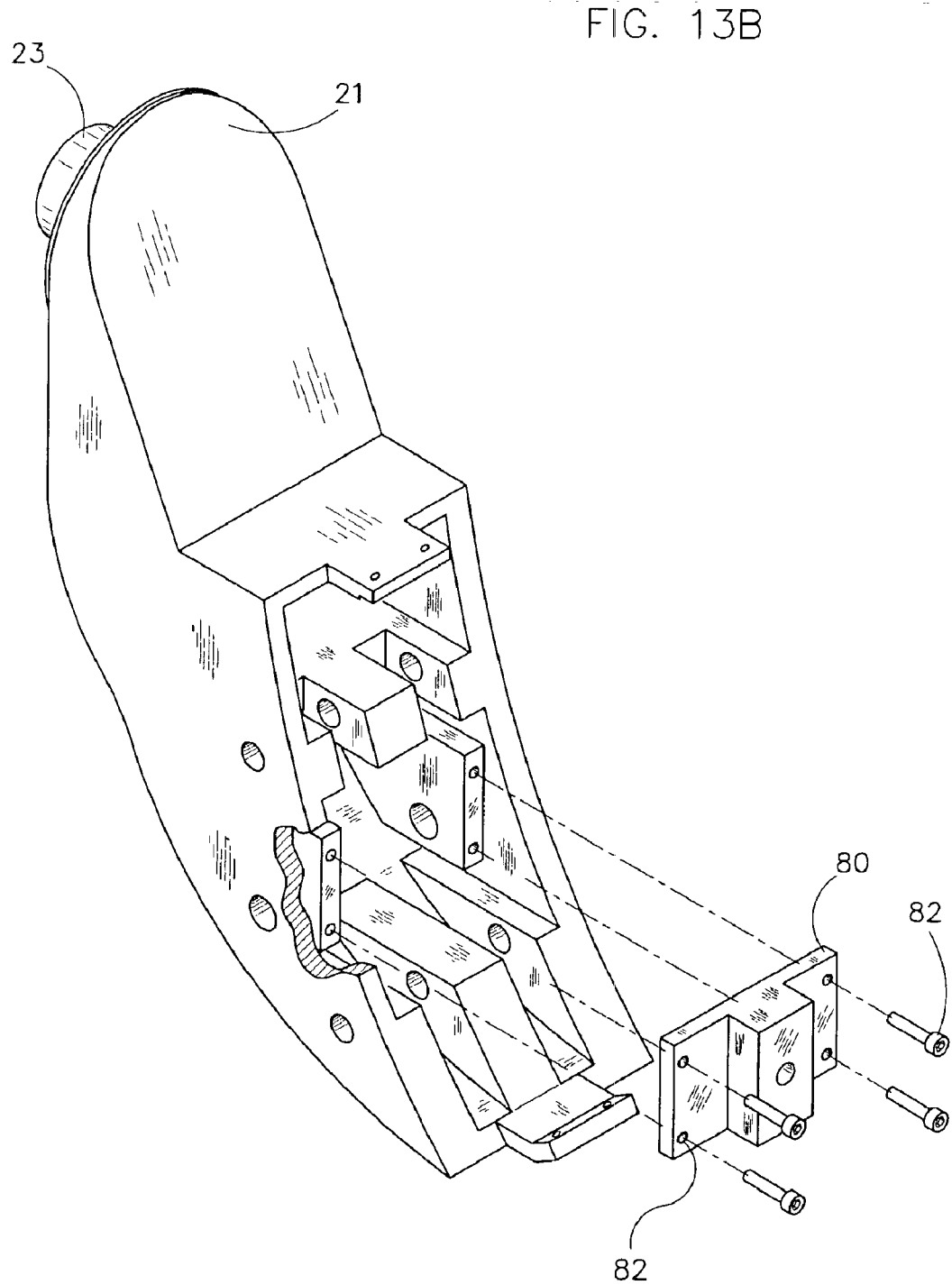
FIG. 13B is another perspective view of the yoke illustrated in FIG. 13A and showing an exploded view of the brake plunger apparatus.

Although the lower portion of the yoke is hollow, it does not lack for strength. As best seen in FIG. 13B, the present invention provides for a brake plate 80. The brake plate 80 is attached to the yoke 20 using a plurality of bolts 82 through a plurality of aperture 84 in the brake plate 80. Thus the brake plate 80 provides lateral reinforcement so that when the C-arm 100 is rotated the yoke 20 does not deform.

Below the stub 23, the yoke 20 gradually increases in cross section. Toward the second end 22 of the yoke 20, the yoke 20 gradually decreases in cross section. Changes in cross section throughout the yoke 20 are gradual to avoid stress concentrations. Additionally, the lower portion of the yoke 20 is hollow to provide for placement of an adjustable brake 24 within the yoke 20 itself. The brake 24 is used to lock the C-arm 100 in place relative to the yoke 20.

The sides of the yoke 20 have a plurality of pivot holes 26. These pivot holes 26 are used to attach the bearings 27 to the yoke 20. The bearings in turn support the C-arm 100 and permit rotation of the C-arm 100 around the outside of the C.

In general, decreasing the bearing span of the yoke 20 increases the overscan capability of the C-arm 100. Unfortunately, decreasing the bearing span also has obvious adverse effects on the stability of the C-arm 100. Another concern is the desire to avoid pinch points between the x-ray source 12 and the yoke 20 and between the image detector 14 and the yoke 20, which decreases overscan. The apparatus of the present invention responds to this problem, by providing a device that increases in bearing span by mounting the bearing brackets 27 attached to pivot arms 27, which are in turn attached to pivot holes 26 outside the actual span of the yoke 20.

The C-arm 100 is a generally semicircular apparatus that is held in a rotational sliding position by a series of bearings 27 on second end 22 of the yoke 20. The first end 11 of the C-arm 100 has an x-ray source 14 and the second end 12 of the C-arm 100 has an x-ray detector 16. The C-arm 100 maintains the x-ray source 12 and an image detector 16 in diametrically facing positions.

The C-arm 100 is generally capable of movement in at least two degrees of freedom. The first end of the yoke 20 is permitted to rotate 360 degrees about its connection with the cabinet support. Also, the exterior of the C-arm 100 is permitted to roll along the second end 22 of the yoke 20. Generally, the C-arm 100 is permitted to rotate orbitally around its own axis. The breadth of rotation of the C-arm 100 is limited only by the width of the yoke 20.

Previous yokes required an inch of clearance on each side in order to avoid the possibility of a pinch point. The yoke 20 of the present invention provides a new a unique shape that eliminates the danger of pinch points and decreases the amount of clearance required on both sides of the yoke 20. As shown in FIG. 6, the yoke 20 of the present invention has tapered sides. In effect, the yoke 20 cross section narrows gradually on both the imager and image receptor sides of the yoke 20. Therefore, if a person left a finger in a position in which it may have been pinched by prior devices, it will instead by urged away from the pinch point by a tapered sides. Previous yokes generally ceded this overscan area to a blunt yoke edge and an inch of wasted space for the pinch point. Thus, previous designs failed to have the extensive overscan of the present invention.

Figure 7:
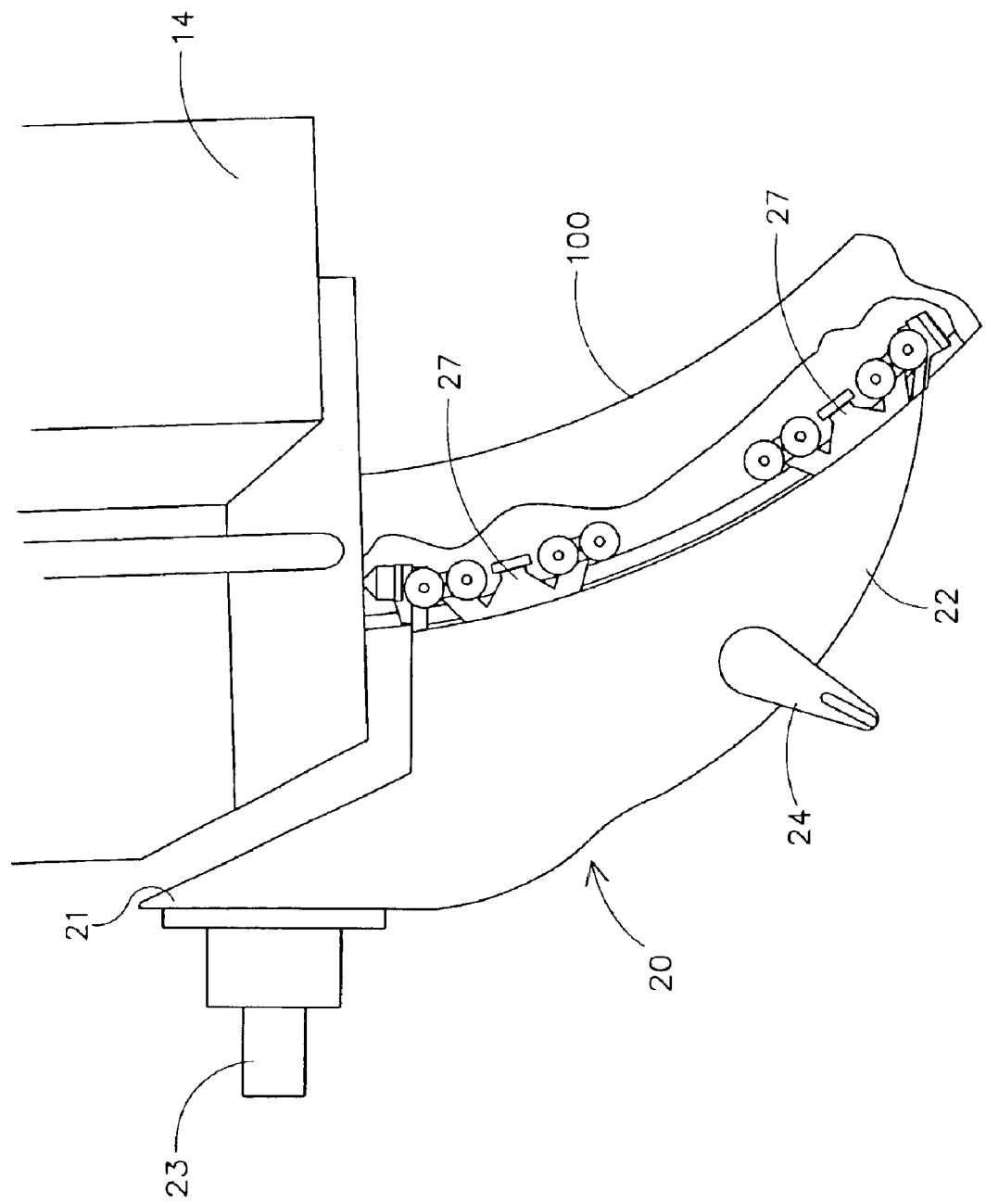
FIG. 7 is another enlarged and partially segmented left side elevational view of the x-ray receptor and the yoke used in the present invention.

Stability of the C-arm 100 is also important to the device of the present invention. The primary way to assure stability of the C-arm 100 is to maximize bearing span. The device of the present invention actually employs a bearing design that exceeds the width of the yoke 20. Obviously, the bearing should not come into contact with the x-ray imager 12 or the imager receptor 14 lest they be damaged. Therefore, the yoke 20 of the present invention provides for an imager lip fender 200 and a TTH lip fender 210 as shown in FIG. 7.

The imager lip 200, as shown in more detail in FIGS. 11A through 11H, is attached to the yoke 20. The imager lip 200 is generally equipped with a rubber bumper, or tomb, 202 to eliminate mechanical noise when the yoke impacts 20 with the imager 14. The imager lip 200 is generally runs parallel to the yoke 20 with the exception of the end portions 203, 204 of the imager lip 200. Both end portions 203, 204 are curved outwardly to accommodate the bearings 27, which span outside of the actual yoke 20 area on the C-arm 100.

The TTH lip 210, as shown in great detail in FIGS. 12A through 12H, is attached to the image receptor 14 side of the yoke 20. The TTH lip 210 is also equipped with a rubber bumper 212 and runs parallels to the yoke 20. However, as with the imager lip 200, the ends 213, 214 of the TTH lip 210 are curved outwardly to accommodate the bearings on the yoke 20, which span outside of the actual yoke 20 are on the C-arm 100.

Figure 3:
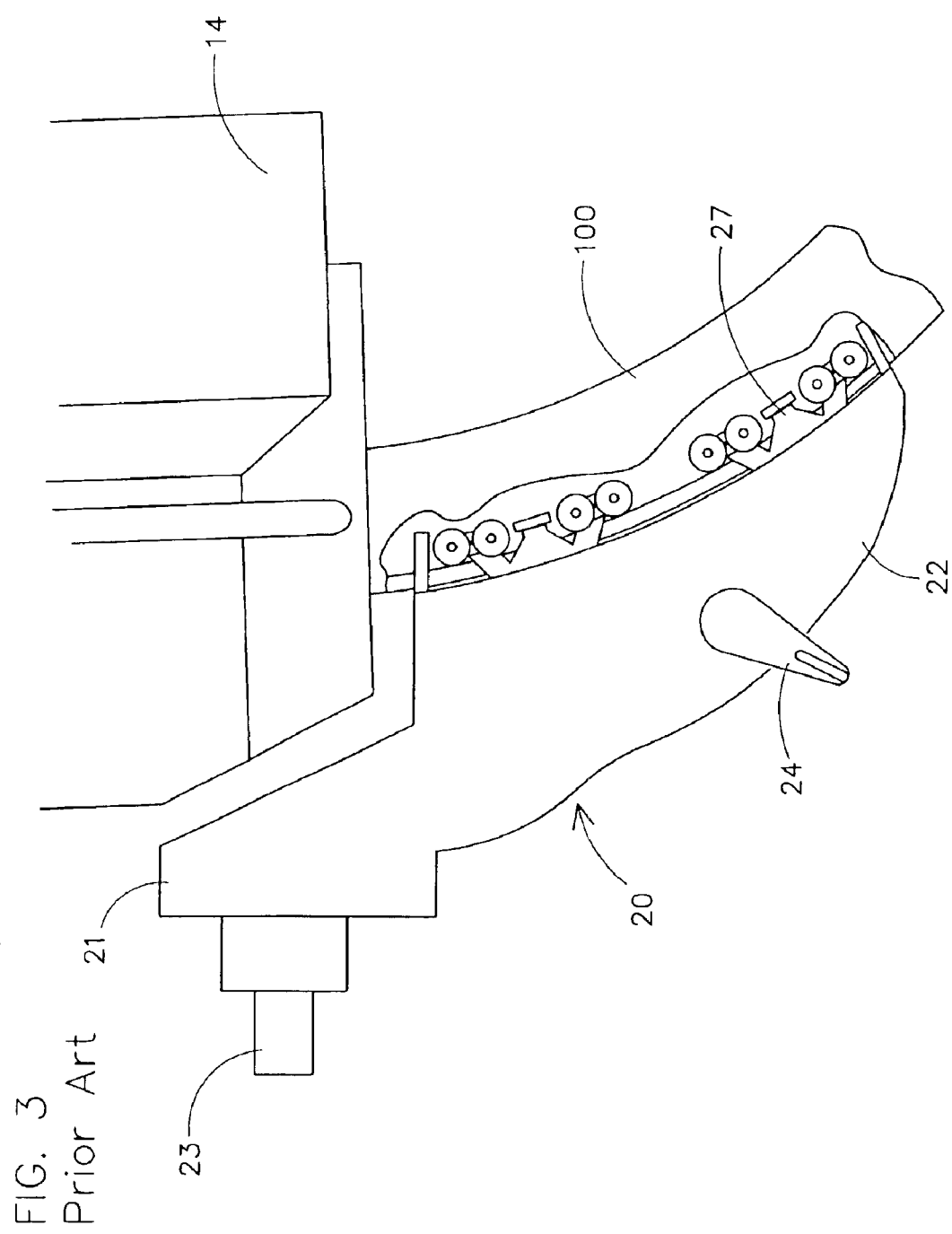
FIG. 3 is another enlarged and partially segmented left side elevational view of the x-ray receptor and yoke typical of the prior art C-arm x-ray machine.
Figure 4:
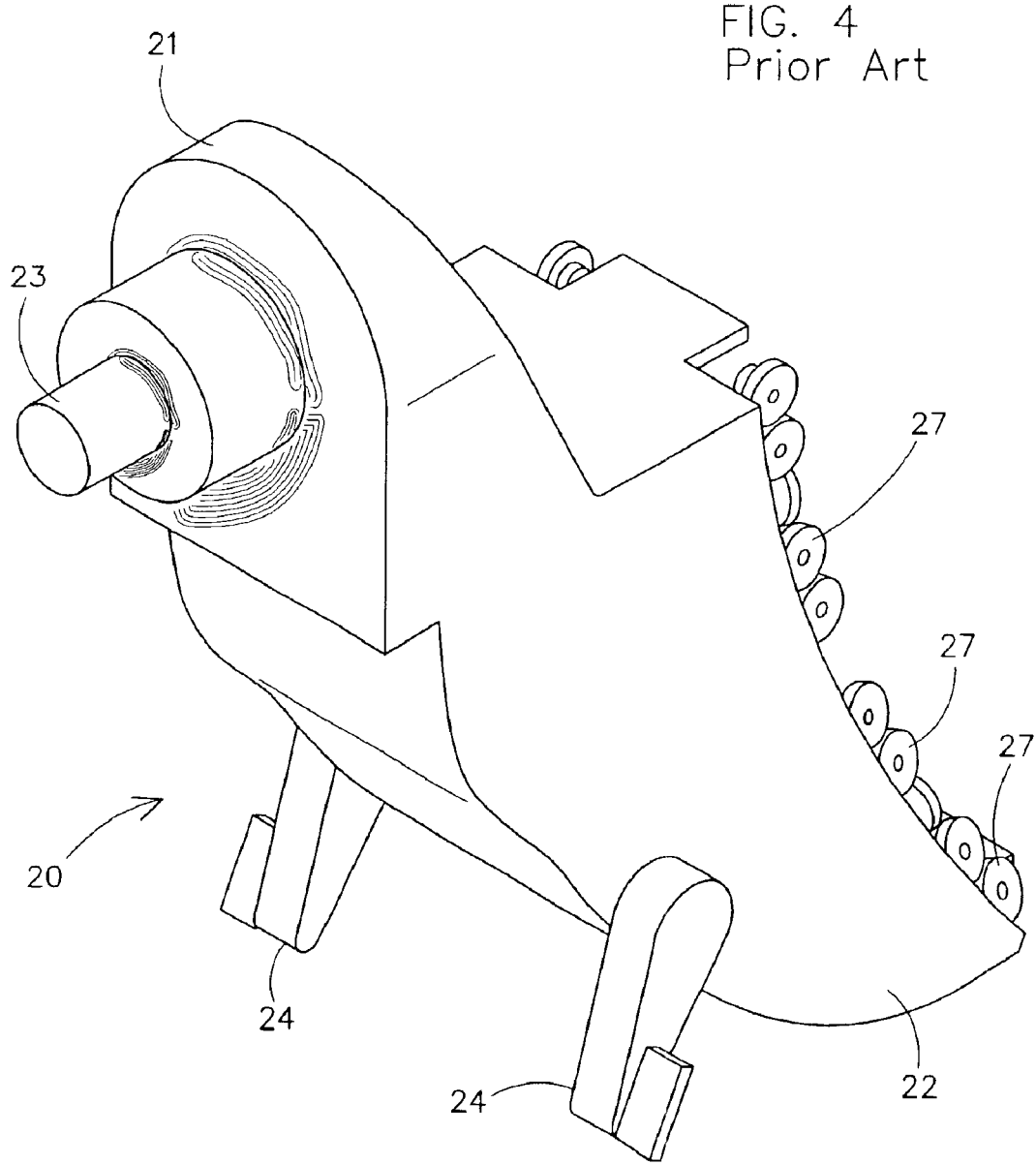
FIG. 4 is a top, left and rear perspective view of a prior art yoke employed in a C-arm x-ray machine.

The advances of the present invention can be best understood by studying the drawings of this invention. In particular, FIG. 6 and FIG. 7 show the increase in overscan provided by the present invention as compared to FIG. 2 and FIG. 3. The improvements in the yoke of the present invention are particularly obvious in comparing prior art example in FIG. 4 and the yoke of FIG. 8. The yoke illustrated in FIG. 8 is obviously shorter, which enables it to fit more easily in compact quarters such as operating rooms. The yoke of FIG. 8 is also lighter than previous yokes which, in general, brings the C-arm's 100 center of gravity closer to the axis of rotation and reduces the amount of effort required to rotate it.

It is to be understood that the invention is not limited to the embodiments set forth herein but that the invention may be carried out in other ways without departure from the spirit of this invention.

10 C-arm x-ray imaging machine
12 x-ray source
14 image receptor
20 yoke
21 first end of the yoke
22 second end of the yoke
23 pin on the first end of the yoke
24 yoke brake
26 pivot holes for bearings
27 bearings, bearing bracket and pivot arm
30 support arm
31 first end of support arm
32 second end of support arm
40 doghouse
50 cross arms
51 first end of the cross arm
52 secod end of the cross arm
53 aperture in the second end of the cross arm
60 support base
70 steel sleeve
71 first end of the sleeve
72 second end of the sleeve
73 sleeve skirt
74 circumference sleeve bolts
75 center sleeve bolt
76 aperture in steel skirt
77 aperture in center of steel sleeve
80 brake plate
82 apertures in brake plate
84 bolts for brake plate
100 C-arm
200 imager lip fender
202 rubber bumper
203 first end of the imager lip
204 second end of the imager lip
210 TTH lip fender
212 bumper
213 first end of the TTH lip fender
214 second end of the TTH lip fender

What is claimed is:

1. A C-arm x-ray apparatus comprising a mobile support base, a doghouse attached to the support base, an extendable cross arm having a first end slidably attached to the doghouse and a second end, a support member having a first end attached to the second end of the cross arm and a second end, the second end of the support arm having a generally circular aperture, a yoke having a first end having a pin that slides within the aperture of the support member wherein the yoke is permitted to rotate, said yoke having a second end, said second end of the yoke being closest to the x-ray source and being tapered down to the C-arm such that when the C-arm is rotated the x-ray source contacts the tapered edge of the yoke thereby eliminating a pinch-point by a gradually funneling of a potentially pinched part away from the diminishing area of the rotating C-arm.

a steel sleeve fitted over the pin on the first end of the yoke attached to the yoke using a plurality of fasteners a C-arm attached to said yoke, an x-ray source, and an image receptor, wherein the imager receptor and the x-ray source are mounted on opposing ends of the C-arm.

2. The apparatus of the claim 1 wherein bearing span is maximized on the image receptor side of the yoke by extending bearings from the side of the yoke and using flexible fenders to cover the bearings.

3. The C-arm x-ray apparatus of claim 2 wherein the C-arm is permitted to rotate up to 45 degrees beyond the vertical configuration.

4. The C-arm x-ray apparatus of claim 3 wherein the yoke is further comprised of a plurality of apertures, a pivot arm for each aperture, and a plurality of bearings supported by each pivot arm, wherein the bearings are permitted to move beyond the yoke to maximize bearing span and are protected by a plurality of fenders extending outwardly from the yoke.

5. A C-arm x-ray apparatus comprising a mobile support base, a doghouse attached to the support base, an extendable cross arm having a first end slidably attached to the doghouse and a second end having a generally circular aperture, a yoke having a first end with a cylindrical pin and a second end, a steel sleeve having a integrally formed circular skirt attached to the first end of the yoke and surrounding the cylindrical pin on the yoke, a C-arm attached to the yoke, an x-ray source, and an image receptor, wherein the image receptor and the x-ray source are mounted on opposing ends of the C-arm.

6. The C-arm x-ray apparatus of claim 5 wherein the steel sleeve is comprised of an integrally formed circular skirt having a plurality of apertures to accommodate bolts to secure the sleeve to the yoke, an open cylindrical area extending upwardly from the circular skirt to accommodate the cylindrical pin of the first end of the yoke, said cylindrical area abruptly tapering to form a smaller cylinder having an aperture designed to accommodate a bolt, and a bolt to secure the steel sleeve to an aperture in the pin.

7. The C-arm x-ray apparatus of claim 6 wherein overscan of the C-arm is maximized by tapering the end of the yoke closest to the x-ray source down to the C-arm such that when the C-arm is rotated, the x-ray source engages the tapered edge of the yoke, thus eliminating a pinchpoint by gradually pushing any potentially pinched part away from the diminishing area of the rotating C-arm.

8. The C-arm x-ray apparatus of claim 7 wherein the bearing span is maximized on the image receptor side of the yoke by extending the bearings from the side of the yoke and using flexible fenders to cover the bearings.

9. The C-arm x-ray apparatus of claim 8 wherein the C-arm is permitted to rotate up to 45 degrees beyond the vertical configuration.

10. The C-arm x-ray apparatus of claim 9 wherein the yoke is further comprised of
  a plurality of apertures,
  a pivot arm for each aperture, and
  a plurality of bearings supported by each pivot arm,
  wherein the bearings are permitted to move beyond the yoke to maximize bearing span and are protected by a plurality of fenders extending outwardly from the yoke.

11. A C-arm x-ray apparatus comprising
  a mobile support base,
  a doghouse attached to the support base,
  an extendable cross arm having a first end slidably attached to the doghouse and a second end having a generally circular aperture,
  an aluminum yoke having a first end with a yoke stub protruding from a generally flat surface, said yoke gradually increasing in cross section and then gradually decreasing in cross section to the second end, said second end providing a curved edge to accommodate the general shape of the C-arm,
  a steel sleeve having an integrally formed circular skirt attached to the first end of the yoke and snugly surrounding the yoke stub, and
  a C-arm attached to the yoke, said C-arm including an x-ray source and an Image receptor, said image receptor and x-ray source being mounted on opposing ends of the C-arm.

12. The C-arm x-ray apparatus of claim 11 wherein the yoke further comprises a hollow portion on the second end of the yoke that houses a brake mechanism.

13. The C-arm x-ray apparatus of claim 12 wherein the steel sleeve is comprised of an integrally formed circular skirt having a plurality of apertures to accommodate bolts to secure the sleeve to the yoke, an open cylindrical area rising up from the circular skirt that accommodates the cylindrical pin of the first end of the yoke, said cylindrical area abruptly tapering to form a smaller cylinder having an aperture designed to accommodate a bolt, said bolt being provided to secure the steel sleeve to en aperture in the pin.

14. The C-arm x-ray apparatus of claim 13 wherein overscan of the C-arm is maximized by tapering the end of the yoke closest to the x-ray source down to the C-arm such that when the C-arm is rotated, the x-ray source engages the tapered edge of the yoke, thus eliminating a pinchpoint by gradually pushing any potentially pinched part away from the diminishing area or the rotating C-arm.

15. The C-arm x-ray apparatus of claim 14 wherein bearing span is maximized on the image receptor side of the yoke by extending the bearings from the side of the yoke and using flexible fenders to cover the bearings.

16. The C-arm x-ray apparatus of claim 15 wherein the C-arm is permitted to rotate up to 45 degrees beyond the vertical configuration.

17. The C-arm x-ray apparatus of claim 16 wherein the yoke is further comprised of
  a plurality of apertures,
  a pivot arm for each aperture, and
  a plurality of bearings supported by each pivot arm,
  wherein the bearings are permitted to move beyond the yoke to maximize bearing span and are protected by a plurality of fenders extending outwardly from the yoke.

18. A C-arm x-ray apparatus comprising
  a mobile support base,
  a doghouse attached to the support base,
  an extendable cross arm having a first end slidably attached to the doghouse and a second end having a generally circular aperture,
  an aluminum yoke having a first end with a yoke stub protruding from a generally flat surface, said yoke gradually increasing in cross section and then gradually decreasing in cross section to the second end, said second end providing a curved edge to accommodate the general shape of the C-arm,
  a steel sleeve comprised of an integrally formed circular skirt having a plurality of apertures to accommodate bolts to secure the sleeve to the yoke, an open cylindrical area rising up from the circular skirt that accommodates the cylindrical pin of the first end of the yoke, said cylindrical area abruptly tapering to form a smaller cylinder having an aperture designed to accommodate a bolt, said bolt to secure the steel sleeve to an aperture in the pin,
  a C-arm attached to the yoke,
  an x-ray source, and
  an image receptor,
  wherein the image receptor and the x-ray source are mounted on opposing ends of the C-arm.

19. The C-arm x-ray apparatus of claim 18 wherein the yoke further comprises a hollow portion on the second end of the yoke that houses a brake mechanism.

20. The C-arm x-ray apparatus of claim 19 wherein overscan of the C-arm is maximized by tapering the end of the yoke closest to the x-ray source down to the C-arm such that when the C-arm is rotated, the x-ray source bumps into the tapered edge of the yoke, thus eliminating a pinchpoint by gradually pushing any potentially pinched part away from the diminishing area of the rotating C-arm.

21. The C-arm x-ray apparatus of claim 20 wherein bearing span is maximized on the image receptor side of the yoke by extending the bearings from the side of the yoke and by using flexible fenders to cover the bearings.

22. The C-arm x-ray apparatus of claim 21 wherein the C-arm is permitted to rotate up to 45 degrees beyond the vertical configuration.

23. A C-arm x-ray machine having
  a mobile support base, a doghouse attached to the support base, an extendable cross arm having a first end slidably attached to the doghouse and a second end having a generally circular aperture, a C-arm, an x-ray source, an image receptor, wherein the image receptor and the x-ray source are mounted on opposing ends of the C-arm, a yoke comprising an aluminum yoke having a first end with a yoke stub protruding from a generally flat surface, said yoke gradually increasing in cross section and then gradually decreasing in cross section to the second end, said second end providing a curved edge to accommodate the general shape of the C-arm, a steel sleeve comprised of an integrally formed circular skirt having a plurality of apertures to accommodate bolts to secure the sleeve to the yoke, an open cylindrical area rising up from the circular skirt that accommodates the cylindrical pin of the first end of the yoke, said cylindrical area abruptly tapering to form a smaller cylinder having an aperture designed to accommodate a bolt, said bolt to secure the steel sleeve to an aperture in the pin, a plurality of apertures, a pivot arm for each aperture, and a plurality of bearings supported by each pivot arm, wherein the bearings are permitted to move beyond the yoke to maximize bearing span and are protected by a plurality of fenders extending outwardly from the yoke.

* * * * *

UNITED STATES PATENT AND TRADEMARK OFFICE
CERTIFICATE OF CORRECTION

PATENT NO. : 6,866,418 B2
DATED : March 15, 2005
INVENTOR(S) : Pillai et al.

It is certified that error appears in the above-identified patent and that said Letters Patent is hereby corrected as shown below:

Column 9,
Line 51, "Image" should be replaced with -- image --.
Line 65, "en" should be replaced with -- an --.

Signed and Sealed this

Eleventh Day of October, 2005

JON W. DUDAS
*Director of the United States Patent and Trademark Office*